United States Patent
Yamamoto et al.

(10) Patent No.: US 11,618,699 B2
(45) Date of Patent: Apr. 4, 2023

(54) DIOXANE-DEGRADING BACTERIA-IMMOBILIZED CARRIER, BIODEGRADATION TREATMENT METHOD, AND BIODEGRADATION TREATMENT APPARATUS

(71) Applicants: TAISEI CORPORATION, Tokyo (JP); ORGANO CORPORATION, Tokyo (JP)

(72) Inventors: Norifumi Yamamoto, Tokyo (JP); Jun Kusaka, Tokyo (JP); Atsushi Itagaki, Tokyo (JP); Kazuichi Isaka, Tokyo (JP); Yutaka Tsuda, Tokyo (JP); Masahiro Eguchi, Tokyo (JP)

(73) Assignees: TAISEI CORPORATION, Tokyo (JP); ORGANO CORPORATION, Tokyo (JP)

( * ) Notice: Subject to any disclaimer, the term of this patent is extended or adjusted under 35 U.S.C. 154(b) by 325 days.

(21) Appl. No.: 16/764,814

(22) PCT Filed: Oct. 15, 2018

(86) PCT No.: PCT/JP2018/038312
§ 371 (c)(1),
(2) Date: May 15, 2020

(87) PCT Pub. No.: WO2019/097921
PCT Pub. Date: May 23, 2019

(65) Prior Publication Data
US 2020/0354244 A1      Nov. 12, 2020

(30) Foreign Application Priority Data

Nov. 17, 2017   (JP) .............. JP2017-222164

(51) Int. Cl.
*C02F 3/00* (2006.01)
*C12N 1/20* (2006.01)
*C12N 11/02* (2006.01)

(52) U.S. Cl.
CPC ............. *C02F 3/00* (2013.01); *C12N 1/20* (2013.01); *C12N 11/02* (2013.01)

(58) Field of Classification Search
CPC .. C02F 3/00; C02F 3/104; C02F 3/34; Y02W 10/10; C12R 2001/01; C12N 1/20; C12N 11/02
See application file for complete search history.

(56) References Cited

U.S. PATENT DOCUMENTS

| 10,329,631 B2 * | 6/2019 | Yamamoto ............. C12N 1/205 |
| 2018/0135141 A1 | 5/2018 | Yamamoto et al. | |

FOREIGN PATENT DOCUMENTS

| JP | 2001333767 A | 12/2001 |
| JP | 2008306939 A | 12/2008 |
| JP | 2009183162 A | 8/2009 |
| JP | 2010252779 A | 11/2010 |
| JP | 5877918 B1 | 3/2016 |
| JP | 2017042097 A | 3/2017 |
| JP | 6117450 B1 | 4/2017 |
| JP | 2018094455 A | 6/2018 |
| WO | 2016181802 A1 | 11/2016 |

OTHER PUBLICATIONS

Isaka et al., Journal of Water and Environment Technology, vol. 14, No. 4: 289-301, 2016, Published online Aug. 10, 2016; doi: 10.2965/jwet.15-084.*
Adams et al., Oxidation and biodegradability enhancement of 1,4-dioxane using hydrogen peroxide and ozone, Environ. Sci. Technol., 28 (11), pp. 1812-1818, 1994 (7 pages).
International Search Report (ISR) dated Jan. 15, 2019, issued for International application No. PCT/JP2018/038312. (2 pages).
Notification Concerning Transmittal of International Preliminary Report on Patentability (PCT/IB/326) and Notification of Transmittal of Translation of the International Preliminary Report on Patentability (PCT/IB/338) dated May 28, 2020, with International Preliminary Report on Patentability (PCT/IB/373) and Written Opinion of the International Searching Authority (PCT/ISA/237), for corresponding international application PCT/JP2018/038312 (18 pages).
Saito, Potential of 1,4-dioxane in microbial degradation and groundwater purification applications, AICHI Soil and Groundwater Contamination Countermeasures Study Group, Jun. 1, 2016 (8 pages).
Sei et al., Challenge for biotreatment of groundwater contaminated with 1,4-dioxane by 1,4-dioxane-degrading bacteria, J. Water and Waste water, vol. 53, No. 7, 2011 (4 pages).
Sei et al., Isolation and characterization of bacterial strains that have high ability to degrade 1,4-dioxane as a sole carbon and energy source, Biodegradation, 24, 5, pp. 665-674, 2012 (10 pages).
A Notice of Reasons for Refusal issued by the Japanese Patent Office dated Nov. 22, 2022, for Japanese counterpart application No. 2019-553751. (4 pages).

* cited by examiner

*Primary Examiner* — Kade Ariani
(74) *Attorney, Agent, or Firm* — Law Office of Katsuhiro Arai

(57) ABSTRACT

An object is to provide a degrading bacteria-immobilized carrier on which a 1,4-dioxane-degrading bacterium is supported, as well as a biodegradation treatment method for organic compounds, and a biodegradation treatment apparatus, both using this carrier. As a means for achieving the object, a degrading bacteria-immobilized carrier comprising a porous carrier and a 1,4-dioxane-degrading bacterium supported on the porous carrier, as well as a biodegradation treatment method for organic compounds, and a biodegradation treatment apparatus, both using this carrier, are provided.

8 Claims, 1 Drawing Sheet

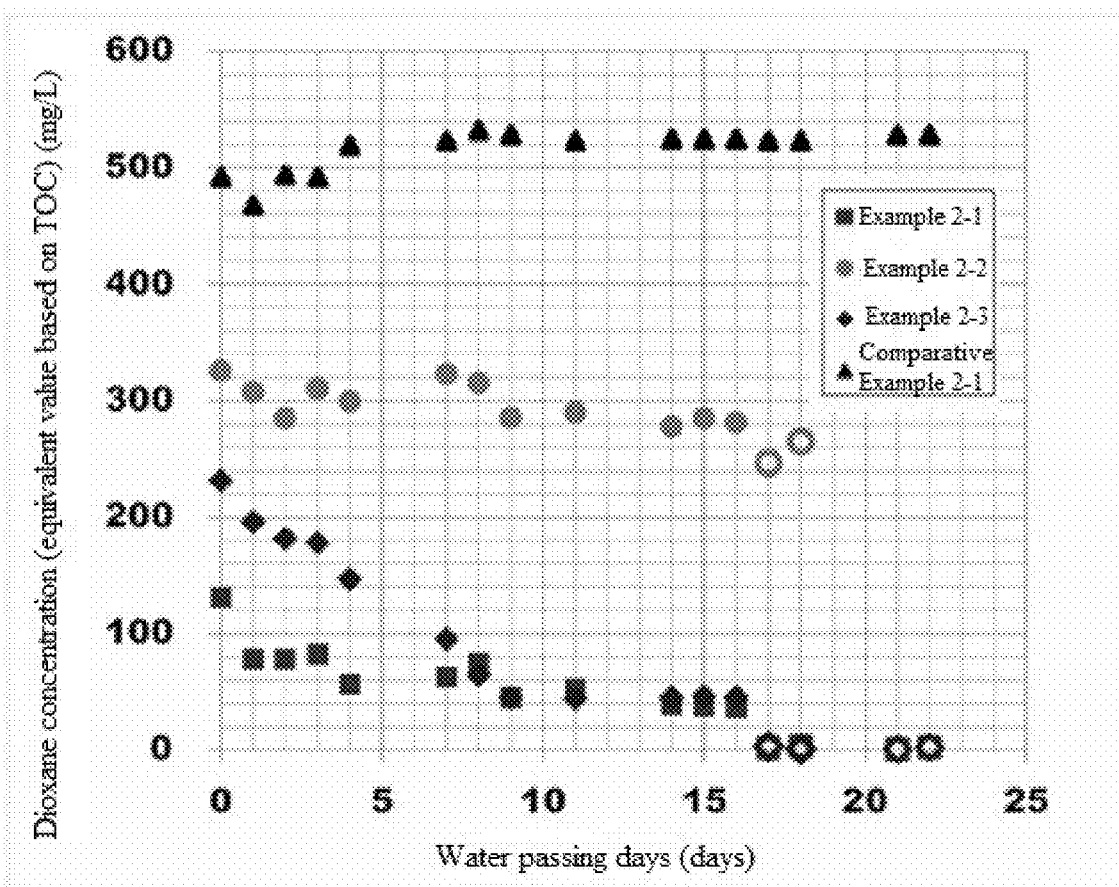

DIOXANE-DEGRADING BACTERIA-IMMOBILIZED CARRIER, BIODEGRADATION TREATMENT METHOD, AND BIODEGRADATION TREATMENT APPARATUS

CROSS-REFERENCE TO RELATED APPLICATIONS

This application is the U.S. National Phase under 35 U.S.C. § 371 of International Application PCT/JP2018/038312, filed Oct. 15, 2018, which claims priority to Japanese Patent Application No. JP2017-222164, filed Nov. 17, 2017. The International Application was published under PCT Article 21(2) in a language other than English.

TECHNICAL FIELD

The present invention relates to a carrier to which a 1,4-dioxane-degrading bacterium is fixed, as well as a biodegradation treatment method for contaminated water, and a biodegradation treatment apparatus, both utilizing this carrier.

BACKGROUND ART 1,4-dioxane is a cyclic ether expressed by Formula (1) below. 1,4-dioxane has excellent compatibility with water and organic solvents and is primarily used as a reaction medium in organic synthesis.

[Chem. 1]

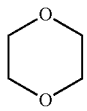

(1)

In 2010, Japan manufactured/imported approx. 4,500 t/year of 1,4-dioxane, of which approx. 300 t/year are estimated to have been released into the environment during the year. As it is soluble in water, 1,4-dioxane will diffuse to wide areas once released into a water environment. Also, removing 1,4-dioxane from water is difficult because its volatility, adsorptivity on solids, photodegradability, hydrolizability and biodegradability are all low. Since 1,4-dioxane has acute toxicity and chronic toxicity, and its carcinogenicity is also pointed out, there are concerns that contamination of water environments by 1,4 dioxane will negatively affect humans, animals, and plants. Accordingly, 1,4-dioxane is regulated in Japan under tap water quality standards (not to exceed 0.05 mg/L), environmental standards (not to exceed 0.05 mg/L) and wastewater standards (not to exceed 0.5 mg/L).

In addition, Non-patent Literature 1 reports that industrial effluent containing 1,4-dioxane also contains 1,3-dioxolane, 2-methyl-1,3-dioxolane and other cyclic ethers in addition to 1,4-dioxane. In particular, 1,3-dioxolane has been confirmed to have acute toxicity and other toxicities, which means that wastewater, etc., containing 1,3-dioxolanes must be treated properly.

Methods are being sought for treating water containing 1,4-dioxane and other cyclic ethers at low cost and in a stable manner, and Patent Literature 1 and Non-patent Literature 2 propose 1,4-dioxane treatment using 1,4-dioxane-degrading bacteria. 1,4-dioxane-degrading bacteria are largely classified into two types: bacteria that degrade 1,4-dioxane as a sole carbon source (assimilating bacteria); and bacteria that can degrade 1,4-dioxane in the presence of tetrahydrofuran or other specific matrix (co-metabolic bacteria). Accordingly, it is efficient, when treating 1,4-dioxane contained in groundwater, wastewater, etc., with 1,4-dioxane-degrading bacteria, to utilize assimilating bacteria that do not require any specific substrate to be added.

Assimilating bacteria are further classified into the inducible type and the constitutive type depending on whether or not a 1,4-dioxane-degrading enzyme is induced. As described in Non-patent Literature 3, inducible 1,4-dioxane-degrading bacteria produce/secrete a degrading enzyme when 1,4-dioxane or other inducing substance is present, and must therefore be acclimated before they can be used in treating 1,4-dioxane. On the other hand, constitutive 1,4-dioxane-degrading bacteria are constantly producing a degrading enzyme and can be used in treating 1,4-dioxane immediately without acclimation.

The inventors of the present invention proposed, in Patent Literature 2, a method for culturing 1,4-dioxane-degrading bacteria wherein a culture medium containing diethylene glycol is used to grow 1,4-dioxane-degrading bacteria. Since 1,4-dioxane-degrading bacteria have an excellent ability to utilize diethylene glycol as a carbon source compared to other microorganisms, they can be grown preferentially under conditions that allow for habitation of other microorganisms, without performing sterilization treatment, when a culture medium containing diethylene glycol is used.

Furthermore, the inventors of the present invention report, in Patent Literature 3, strain N23 which is a constitutive 1,4-dioxane-degrading bacterium. Strain N23 exhibits the highest 1,4-dioxane maximum specific degradation rate among the constitutive 1,4-dioxane-degrading bacteria reported to date, and is very promising in the area of biodegrading 1,4-dioxane and other cyclic ethers.

Strain N23 has an excellent ability to utilize 1,4-dioxane, ethylene glycol, diethylene glycol, and 1,4-butane diol as carbon sources, compared to microorganisms having no 1,4-dioxane-degrading ability.

BACKGROUND ART LITERATURE

Patent Literature

Patent Literature 1: Japanese Patent Laid-open No. 2008-306939
Patent Literature 2: Japanese Patent No. 5877918
Patent Literature 3: Japanese Patent No. 6117450

Non-Patent Literature

Non-patent Literature 1: C D. Adams, P A. Scanlan and N D. Secrist: Oxidation and biodegradability enhancement of 1,4-dioxane using hydrogen peroxide and ozone, Environ. Sci. Technol., 28 (11), pp. 1812-1818, 1994.
Non-patent Literature 2: Kazunari Sei and Michihiko Ike: Challenge for biotreatment of groundwater contaminated with 1,4-dioxane by 1,4-dioxane-degrading bacteria, J. Water and Waste water, Vol. 53, No. 7, 2011.
Non-patent Literature 3: K. Sei, K. Miyagaki, T. Kakinoki, K. Fukugasako, D. Inoue and M. Ike: Isolation and characterization of bacterial strains that have high ability to degrade 1,4-dioxane as a sole carbon and energy source, Biodegradation, 24, 5, pp. 665-674, 2012.

SUMMARY OF THE INVENTION

Problems to be Solved by the Invention

An object of the present invention is to provide a degrading bacteria-immobilized carrier on which a 1,4-dioxane-degrading bacterium (hereinafter also referred to as "degrading bacterium") is supported, as well as a biodegradation treatment method for organic compounds, and a biodegradation treatment apparatus, both using this carrier.

Means for Solving the Problems

1. A degrading bacteria-immobilized carrier characterized in that it comprises: a porous carrier; and a 1,4-dioxane-degrading bacterium supported on the porous carrier.
2. A degrading bacteria-immobilized carrier according to 1, characterized in that the porous carrier has a specific surface area of 3,000 $m^2/m^3$ or greater but no greater than 60,000 $m^2/m^3$.
3. A degrading bacteria-immobilized carrier according to 1 or 2, characterized in that the porous carrier is hydrophobic.
4. A degrading bacteria-immobilized carrier according to any one of 1 to 3, characterized in that the 1,4-dioxane-degrading bacterium is of the *Pseudonocardia* species.
5. A degrading bacteria-immobilized carrier according to any one of 1 to 4, characterized in that the 1,4-dioxane-degrading bacterium is strain N23 that has been deposited under Accession No. NITE BP-02032.
6. A method for manufacturing a degrading bacteria-immobilized carrier comprising a porous carrier and a 1,4-dioxane-degrading bacterium supported on the porous carrier, characterized in that the porous carrier is introduced to a liquid culture medium while culturing therein the 1,4-dioxane-degrading bacterium.
7. A biodegradation treatment method characterized in that an organic compound is biodegradation-treated using a degrading bacteria-immobilized carrier of any one of 1 to 5.
8. A biodegradation treatment method according to 7, characterized in that the organic compound contains a cyclic ether.
9. A biodegradation treatment method according to 7 or 8, characterized in that the organic compound contains at least one type selected from 1,4-dioxane, 1,3-dioxolane, 2-methyl-1,3-dioxolane, and tetrahydrofuran.
10. A biodegradation treatment method according to any one of 7 to 9, characterized in that it is a fed-batch process.
11. A biodegradation treatment method according to any one of 7 to 9, characterized in that it is a continuous process.
12. A biodegradation treatment apparatus characterized by biodegradation-treating an organic compound using a degrading bacteria-immobilized carrier of any one of 1 to 5.
13. A biodegradation treatment apparatus according to 12, characterized in that the organic compound contains a cyclic ether.
14. A biodegradation treatment apparatus according to 12 or 13, characterized in that the organic compound contains at least one type selected from 1,4-dioxane, 1,3-dioxolane, 2-methyl-1,3-dioxolane, and tetrahydrofuran.
15. A biodegradation treatment apparatus according to any one of 12 to 14, characterized in that it performs a fed-batch process.
16. A biodegradation treatment apparatus according to any one of 12 to 14, characterized in that it performs a continuous process.

Effects of the Invention

By using the degrading bacteria-immobilized carrier proposed by the present invention, outflow of the degrading bacterium can be prevented, and a high treatment activity can be maintained during the biodegradation treatment of organic compounds. By using the degrading bacteria-immobilized carrier proposed by the present invention, outflow of the degrading bacterium can be prevented, and a high bacterial body concentration can be retained, even in a continuous process. The degrading bacteria-immobilized carrier proposed by the present invention permits biodegradation treatment with a high-density degrading bacterium, which allows for reduction in aeration tank capacity.

Carriers whose porous carrier has a specific surface area of 3,000 $m^2/m^3$ or greater but no greater than 60,000 $m^2/m^3$, and carriers whose porous carrier is constituted by a hydrophobic material, allow for easy attachment of degrading bacteria and can support a large quantity of bacterial bodies.

Strain N23 has an excellent property of biodegrading organic compounds and can also degrade 1,4-dioxane of high to low concentrations, and therefore carriers to which strain N23 is fixed can demonstrate a stable treatment ability even when the organic compound concentration in the treating water varies.

BRIEF DESCRIPTION OF THE DRAWINGS

FIG. 1 A diagram showing how the dioxane concentration in wastewater changes over time during the continuous process in Experiment 2.

MODE FOR CARRYING OUT THE INVENTION

The present invention is explained in detail below.

The degrading bacteria-immobilized carrier proposed by the present invention comprises a porous carrier and a 1,4-dioxane-degrading bacterium supported on the porous carrier.

Porous Carrier

A porous carrier is a granular and solid carrier having multiple holes inside the carrier, and is different from a general fibrous carrier. The shape of the porous carrier is not limited in any way and may be, for example, a cube shape, rectangular solid shape, hexagonal prism, or other polygonal prism shape, cylindrical shape, or spherical shape, for example. A cube shape or rectangular solid shape is preferred for ease of manufacturing of the carrier.

The carrier size of the porous carrier is not limited in any way, but it is preferably 1 $mm^3$ or greater but no greater than 1,000 $mm^3$, or more preferably in a range of 100 $mm^3$ or greater but no greater than 1,000 $mm^3$. If the carrier size of the porous carrier is smaller than 1 $mm^3$, the screen separating the carrier may be clogged; if it exceeds 1,000 $mm^3$, on the other hand, the specific surface area may decrease to a point where the degrading bacterium can no longer be retained sufficiently. It should be noted that the carrier size of the porous carrier refers to the average value of volume, of at least 10 carriers, calculated according to their shape based on the values measured thereabout using a caliper, microscope, etc.

The average diameter of the holes in the porous carrier is not limited in any way, but one whose average hole diameter is in a range of 20 μm or greater but no greater than 2,000 μm may be used, for example. If the average diameter of the holes is smaller than 20 μm, the air permeability of the carrier may drop, resulting in lower flowability. If the average diameter of the holes exceeds 2,000 μm, on the other hand, fixing of the degrading bacterium may become difficult. It should be noted that the average diameter of the holes in the porous carrier refers to the average value of the opening diameters, measured with a caliper, microscope, etc., of at least 30 hole openings that are present on the carrier surface.

Preferably the specific surface area of the porous carrier per specific volume of carrier is 3,000 m$^2$/m$^3$ or greater but no greater than 60,000 m$^2$/m$^3$. If the specific surface area is smaller than 3,000 m$^2$/m$^3$, the degrading bacterium may not be retained sufficiently. If the specific surface area is greater than 60,000 m$^2$/m$^3$, on the other hand, the carrier may lift and flow out of the treatment tank easily. The specific surface area is more preferably 4,000 m$^2$/m$^3$ or greater but no greater than 55,000 m$^2$/m$^3$, or yet more preferably 4,500 m$^2$/m$^3$ or greater but no greater than 50,000 m$^2$/m$^3$. It should be noted that the specific surface area of the porous carrier can be calculated according to the BET gas adsorption method using nitrogen gas.

Preferably the porosity of the porous carrier is 50% or higher but no higher than 99%. If the porosity of the porous carrier is lower than 50%, the attached quantity of degrading bacterium may become insufficient. If the porosity exceeds 99%, on the other hand, the air permeability of the carrier may drop, resulting in lower flowability.

The porosity of the porous carrier is calculated using the formula below, by measuring the specific gravity of the subject carrier:

Porosity (%)={1−(Specific gravity/True specific gravity)}×100

Specific gravity: Measured value of specific gravity of the subject carrier

True specific gravity: Specific gravity of the subject carrier material (Literature value, such as 1.20 in the case of polyurethane)

For the porous carrier, any material may be used without limitation and, for example, a sponge made of polyurethane resin, polyethylene, polypropylene, or other polyolefin resin, polyester resin, cellulose resin, vinyl chloride, etc., or gel made of polyvinyl alcohol, alginic acid, polyethylene glycol, etc., may be used. In particular, a porous carrier made of a hydrophobic material is preferred, as it provides an excellent property of attaching the degrading bacterium. This is probably because the degrading bacterium forms a biofilm constituted by a hydrophobic viscous substance, although its composition is unknown. Here, a hydrophobic carrier refers to a carrier that will not sediment in deionized water within 24 hours of being introduced thereto, while a hydrophilic carrier refers to a carrier that will sediment in deionized water within 24 hours of being introduced thereto. Such hydrophobic materials include polyurethane resins, polyethylene, polypropylene, and other polyolefin resins, polyester resins, and cellulose resins.

1,4-dioxane-Degrading Bacterium

The degrading bacterium used under the present invention is not limited in any way, and those belonging to the *Mycobacterium* sp., *Pseudonocardia* sp., *Afipia* sp., *Rhodococcus* sp., *Flavobacterium* sp., *Methylosinus* sp., *Burkholderia* sp., *Ralstonia* sp., *Cordyceps* sp., *Xanthobacter* sp., *Acinetobacter* sp., etc., may be used. Among these, those belonging to the *Mycobacterium* sp. or *Pseudonocardia* sp. are preferred. Also, while any of constitutive assimilating bacteria, inducible assimilating bacteria, and co-metabolic bacteria may be used, assimilating bacteria are preferred because they require no inducing substance, and constitutive assimilating bacteria are more preferred because they need not be acclimated.

Specific examples include *Pseudonocardia* sp. N23, *Mycobacterium* sp. D11, *Pseudonocardia* sp. D17, *Mycobacterium* sp. D6, *Pseudonocardia dioxanivorans* CB1190, *Afipia* sp. D1, *Mycobacterium* sp. PH-06, *Pseudonocardia benzenivorans* B5, *Flavobacterium* sp., *Pseudonocardia* sp. ENV478, *Pseudonocardia tetrahydrofuranoxydans* K1, *Rhodococcus ruber* T1, *Rhodococcus ruber* T5, *Methylosinus trichosporium* OB3b, *Mycobacterium vaccae* JOB5, *Burkholderia cepacia* G4, *Pseudomonas mendocina* KR1, *Pseudonocardia tetrahydrofuranoxydans* K1, *Ralstonia pickettii* PKO1, *Rhodococcus* sp. RR1, *Acinetobacter Baumannii* DD1, *Rhodococcus* sp. 219, *Pseudonocardia antarctica* DVS 5a1, *Cordyceps sinensis* A, *Rhodococcus aetherivorans* JCM14343, etc. Among these, *Pseudonocardia* sp. N23, which is a constitutive assimilating bacterium of excellent degrading ability, is preferred.

*Pseudonocardia* sp. N23 (hereafter referred to as "strain N23") has been internationally deposited, effective Apr. 10, 2015, with the National Institute of Technology and Evaluation's Patent Microorganisms Depositary (NPMD) (2-5-8 Kazusakamatari, Kisarazu-shi, Chiba, Japan (Postal Code 292-0818)) under Accession No. NITE BP-02032.

Strain N23 is Gram positive and catalase positive. Strain N23 has the highest 1,4-dioxane maximum specific degradation rate among the constitutive 1,4-dioxane-degrading bacteria reported to date, the value of which is equal to or greater than the corresponding rates of inducible 1,4-dioxane-degrading bacteria. Also, strain N23 can degrade 1,4-dioxane to an extremely low concentration of 0.017 mg/L or below, and treat 1,4-dioxane of as high a concentration as approx. 5,200 mg/L.

Degrading Bacteria-Immobilized Carrier

How the 1,4-dioxane-degrading bacterium should be supported on the porous carrier to manufacture the degrading bacteria-immobilized carrier proposed by the present invention, is not limited in any way; however, a method whereby a porous carrier is introduced to a liquid culture medium in which the 1,4-dioxane-degrading bacterium is being cultured, is simple and convenient.

The method for culturing the 1,4-dioxane-degrading bacterium is not limited in any way, but since 1,4-dioxane-degrading bacteria have lower proliferation potential compared to other microorganisms (hereinafter referred to as "bacteria"), normal culturing methods are likely to cause bacterial contamination. Accordingly, preferred is the culturing method that uses a culture medium containing diethylene glycol (Patent Literature 2), or, if the degrading bacterium is strain N23, the culturing method that uses a culture medium containing at least one type selected from 1,4-dioxane, glyoxylic acid, glycolic acid, ethylene glycol, diethylene glycol, 1,4-butane diol, 1-butanol, tetrahydrofuran, glucose, and acetic acid (Patent Literature 3), each proposed by the inventors of the present invention.

The degrading bacteria-immobilized carrier proposed by the present invention may also be obtained by introducing the porous carrier into an aeration tank in which biodegradation treatment of the organic compound using the 1,4-dioxane-degrading bacterium is already underway. In this case, preferably the porous carrier is introduced in the organic-compound biodegradation treatment step in the fed-batch process mentioned below, in order to prevent outflow of the degrading bacterium.

Biodegradation Treatment Method and Biodegradation Treatment Apparatus

The biodegradation treatment method and biodegradation treatment apparatus proposed by the present invention are characterized in that an organic compound is biodegradation-treated using a degrading bacteria-immobilized carrier comprising a porous carrier and a 1,4-dioxane-degrading bacterium supported on the porous carrier.

The target of biodegradation treatment may be, for example, groundwater, factory effluent or other contaminated water, or contaminated soil at an illegal damping site, each containing organic compounds. It should be noted that, when purifying contaminated soil, the soil is washed with water beforehand to change to water phase the target organic compound to be treated, so as to treat the soil as contaminated water.

Under the biodegradation treatment method and biodegradation treatment apparatus proposed by the present invention, not much of the dioxane-degrading bacterium flows out with the wastewater following the biodegradation treatment because the degrading bacterium is fixed to the carrier, and consequently the concentration of the degrading bacterium in the treatment tank can be kept at a high level. As a result, the capacity of the treatment tank in which biodegradation treatment is performed can be reduced.

The organic compound to be biodegradation-treated is not limited in any way so long as it is an organic compound that can be degraded, or used as a carbon source, by the 1,4-dioxane-degrading bacterium. Examples include 1,4-dioxane, 1,3-dioxolane, 2-methyl-1,3-dioxolane, tetrahydrofuran and other cyclic ethers, ethylene glycol, diethylene glycol, 1,4-butane diol, and the like.

The biodegradation treatment method using the degrading bacteria-immobilized carrier proposed by the present invention is not limited in any way, but it may be implemented by, for example, a so-called "fed-batch process" in which (1) a biodegradation treatment step targeting the organic compound in contaminated water, (2) a draining step in which the degrading bacteria-immobilized carrier is settled out and only the supernatant of treated water is drained, and (3) a contaminated water introduction step in which new contaminated water is introduced, are repeated in the order of (1)→(2)→(3)→(1)→ . . . , or by a continuous process in which equal amounts of contaminated water and treated water are introduced upstream/drained downstream continuously. In a fed-batch process, the biodegradation treatment rate can be kept at a high level because the initial contaminant concentration in the aeration tank is high. In a continuous process, an existing wastewater treatment facility can be used as is.

Under the biodegradation treatment method and biodegradation treatment apparatus proposed by the present invention, the porous carrier quantity relative to the aeration tank capacity is in a range of preferably 5% or more but no more than 50%, or more preferably 10% or more but no more than 40%, to the water to be treated based on apparent volume. If this porous carrier quantity is less than 5%, the quantity of dioxane-degrading bacterial bodies may become insufficient; if the porous carrier quantity is more than 50%, on the other hand, the flowability of the porous carrier may drop.

EXAMPLES

The present invention is explained more specifically in detail below by citing examples and a comparative example; it should be noted, however, that the present invention is not limited to the following examples.

Experiment 1: Fed-Batch Process

Well water was adjusted to contain 1,000 mg/L of 1,4-dioxane, 20 mg/L of ammonium sulfate in nitrogen concentration, and 5 mg/L of potassium dihydrogen phosphate in phosphorous concentration, for use as test water.

The following three types of porous carriers were used:
Carrier A: Polyurethane porous carrier. Hydrophobic. Cube shape (7-mm square).
Average diameter of holes: 525 μm (measured values: 500 to 550 μm)
Specific surface area: 5,000 $m^2/m^3$
Porosity: 95.0%
Carrier B: Polyurethane porous carrier. Hydrophilic. Cube shape (10-mm square).
Average diameter of holes: 1,500 μm (measured values: 1,000 to 2,000 μm)
Specific surface area: 1,000 $m^2/m^3$
Porosity: 96.5%
Carrier C: Polyvinyl alcohol porous carrier. Hydrophilic. Cube shape (7-mm square).
Average diameter of holes: 80 μm (measured values: 70 to 90 μm)
Specific surface area: 46,000 $m^2/m^3$
Porosity: 89%

It should be noted that the specific surface areas of the carriers were calculated according to the BET gas adsorption method using nitrogen gas, using a high-precision fully automated gas adsorption apparatus (apparatus name: BEL-SORP36, manufactured by BEL Japan Inc. (current name: MicrotracBEL Corp.)).

For the 1,4-dioxane-degrading bacterium, strain N23 was used.

Strain N23 was cultured for 2 weeks using an MGY culture medium (Malt Extract: 10 g/L, Glucose: 4 g/L, Yeast Extract: 4 g/L, pH: 7.3). This culture solution was centrifuged for 3 minutes at 10,000×g and 4° C. for harvesting, and then washed twice using an inorganic salt culture medium (composition of culture medium: $K_2HPO_4$: 1 g/L, $(NH_4)_2SO_4$: 1 g/L, NaCl: 50 mg/L, $MgSO_4.7H_2O$: 200 mg/L, $FeCl_3$:10 mg/L, $CaCl_2$): 50 mg/L, pH: 7.3), and the resulting bacterial bodies were used.

Example 1

The test water was added to a reaction column of 2.2 L in volumetric capacity, to approx. one-third the volumetric capacity. To carrier A that had been weighed to 30% in apparent volume with respect to the volumetric capacity of the reaction column, strain N23 (inoculated solution washed/adjusted using 0.85% saline solution (bacterial body concentration 2,000 mg/L)) was added by 0.1 L and blended under light agitation, after which all remaining quantity was added to the reaction column. The reaction column was filled up with the test water, and then aerated at room temperature (21 to 22° C.) from below the reaction column for 48 hours at 1.0 L/min, to obtain a degrading bacteria-immobilized carrier.

Next, the aeration was stopped for 1 hour to let the degrading bacteria-immobilized carrier to sediment. One half the quantity of the supernatant was discarded and replaced with fresh test water, after which aeration was performed for 24 hours at 1.0 L/min.

Now, the test water comprises well water to which 1,4-dioxane, etc., have been added, and almost the entire quantity of total organic carbons (TOC) present in the test water are derived from dioxane. Accordingly, the TOC concentration in the treated water was measured over time using a total organic carbon analyzer (TOC-LCPN model, manufactured by Shimadzu Corporation) and the equivalent values obtained through the conversion formula below were used to evaluate the dioxane concentrations (equivalent), while the rates of decrease in dioxane were obtained based on the value of initial dioxane concentration (equivalent):

Conversion formula: Dioxane concentration (equivalent)(mg/L)=TOC concentration (mg/L)/0.545

Example 2

Same as Example 1, except that carrier B was used.

Example 3

Same as Example 1, except that carrier C was used.

Comparative Example 1

A control produced in the same manner as Example 1, except that neither a porous carrier nor strain N23 was added and only aeration was performed.

Visual Observation

Examples 2 and 3 that used hydrophilic carriers B and C were agitated by aeration and began flowing inside the reaction column immediately after the start of aeration. However, bacterial bodies were not seen as infiltrating into the holes in the porous carrier.

In Example 1 that used hydrophobic carrier A, on the other hand, the carrier remained suspended and did not flow up or down immediately after the start of aeration.

After 48 hours, it was confirmed that strain N23 was attached to all of carriers A to C. In addition, the carrier was also confirmed flowing in Example 1, having blended with the water.

Rate of Decrease in Dioxane

The rates of decrease in dioxane from the start, in Examples 1 to 3 and Comparative Example 1, are shown in Table 1.

TABLE 1

| | Rate of decrease in dioxane (%) | | | |
|---|---|---|---|---|
| | Example 1 | Example 2 | Example 3 | Comparative Example 1 |
| Treatment period (h) | | | | |
| Initial concentration mg/L | 939 | 949 | 949 | 1004 |
| 3 | 4.7 | 4.3 | 2.0 | 3.9 |
| 6 | 9.2 | 9.3 | 6.0 | 4.8 |
| 24 | 12.9 | 13.4 | 3.9 | 11.3 |
| 48 | 25.3 | 20.3 | 20.3 | 16.6 |
| Replacement of test water | | | | |
| Initial concentration mg/L | 800 | 866 | 870 | 983 |
| 18 | 36.5 | 20.8 | 14.1 | 6.7 |

In Examples 1 to 3, dioxane decreased at higher rates than in Comparative Example 1, confirming that dioxane was degraded by strain N23. In particular, Example 1 using hydrophobic carrier A that had not flowed due to poor blending with the test water at the start of aeration, exhibited excellent dioxane degradability and recorded the highest rate of decrease in dioxane after 48 hours.

Although strain N23 was added by equal quantities in Examples 1 to 3, the dioxane-degrading activity was significantly different between Example 1 and Examples 2 and 3. This suggests that the degrading bacterium fixed to a hydrophobic porous carrier would demonstrate higher degrading activity than the degrading bacterium fixed to a hydrophilic porous carrier.

Experiment 2: Continuous Process

The apparatus used in Experiment 1 above was employed as is to perform a continuous process. The experiments conducted in the same manner as Examples 1 to 3 and Comparative Example 1 using the same apparatus, are referred to as Examples 2-1 to 2-3 and Comparative Example 2-1, respectively.

Well water was adjusted to contain 500 mg/L of 1,4-dioxane, 20 mg/L of ammonium sulfate in nitrogen concentration, and 5 mg/L of potassium dihydrogen phosphate in phosphorous concentration, for use as simulated wastewater.

A continuous process, which involved aeration at 1.0 L/min with this simulated wastewater passed from the top side to the bottom side of the reaction column at a flow rate of 1.2 mL/min (1,4-dioxane loading: 0.37 to 0.42 kg/m$^3$/day), was performed for 25 days.

Once a day, approx. 15 mL of treated water was collected with a syringe from the top part of the reaction column and filtered through a filtration paper (No. 5C), and then evaluated for 1,4-dioxane concentration in the same manner as in Experiment 1 above. It should be noted that the samples collected on day 20 onward were measured for dioxane concentration using a headspace gas chromatograph mass spectrometer (GC/MS-QP2010 PLUS, TURBOMATRIX HS40, manufactured by Shimadzu Corporation; hereinafter referred to as "GC/MS"), to determine accurate values.

How the dioxane concentration changed over time is shown in FIG. 1. It should be noted that, in FIG. 1, outlined plot marks represent GC/MS-measured values of dioxane.

The treatment performance stabilized the fastest in Example 2-1, with the water quality of treated water stabilizing in around 10 days. This was followed by Example 2-3, where the water quality of treated water stabilized in around 2 weeks. In Examples 2-1 and 2-3, the GC/MS-measured dioxane concentration values ranged from 0.5 to 3 mg/L, corresponding to removal rates of 95% or higher. In Example 2-2, on the other hand, there was little improvement in dioxane removal performance, and the removal rate remained at 40% or so.

When the attachment condition of strain N23 was checked visually after the experiment, the surface color of hydrophobic carrier A used in Example 2-1 had changed from yellow to dark orange, while that of hydrophilic carrier C used in Example 2-3 had changed from white to light brown, confirming that large quantities of strain N23 were attached to the carriers. Also, in Example 2-3, it took a longer time for the water quality to stabilize than in Example 2-1. The reason for this is suspected that, although the carrier used in Example 2-3 is hydrophilic and thus its attaching performance and degrading activity with respect to strain N23 were initially poor, it subsequently attached more strain N23 as the hydrophobic viscous substance produced by strain N23 provided footholds, and eventually demonstrated performance equivalent to what was achieved in Example 2-1 where a hydrophobic carrier was used. On the other hand, carrier B used in Example 2-2 did attach strain N23 but hardly changed its surface color and the attached quantity was small. It is suspected that carrier B demonstrated poor performance of attaching the dioxane-degrading bacterium due to its small specific surface area of 1,000 m$^2$/m$^3$ and large hole diameters.

What is claimed is:

1. A 1,4-dioxane-degrading bacteria-immobilized carrier comprising:
a porous carrier; and
a 1,4-dioxane-degrading bacterium immobilized on the porous carrier,
wherein the porous carrier is hydrophobic and has a specific surface area of 3,000 m$^2$/m$^3$ or greater but no greater than 60,000 m$^2$/m$^3$,
pores of the porous carrier have an average diameter of 20 μm or greater but no greater than 2,000 μm, and
the 1,4-dioxane-degrading bacteria is of a *Pseudonocardia* species.

2. The 1,4-dioxane-degrading bacteria-immobilized carrier according to claim 1, characterized in that the 1,4-dioxane-degrading *Pseudonocardia* species is strain N23 that has been deposited under Accession No. NITE BP-02032.

3. A method for manufacturing the 1,4-dioxane-degrading bacteria-immobilized carrier of claim 1, comprising introducing the porous carrier to a liquid culture medium while culturing therein the 1,4-dioxane-degrading bacteria bacterium.

4. A biodegradation treatment method comprising contacting water contaminated with an organic compound with the 1,4-dioxane-degrading bacteria-immobilized carrier of claim 1.

5. The biodegradation treatment method according to claim 4, characterized in that the organic compound contains a cyclic ether.

6. The biodegradation treatment method according to claim 4, characterized in that the organic compound contains at least one compound selected from the group consisting of 1,4-dioxane, 1,3-dioxolane, 2-methyl-1,3-dioxolane, and tetrahydrofuran.

7. The biodegradation treatment method according to claim 4, characterized by being a fed-batch process.

8. The biodegradation treatment method according to claim 4, characterized by being a continuous process.

* * * * *

UNITED STATES PATENT AND TRADEMARK OFFICE
CERTIFICATE OF CORRECTION

PATENT NO. : 11,618,699 B2
APPLICATION NO. : 16/764814
DATED : April 4, 2023
INVENTOR(S) : Norifumi Yamamoto et al.

It is certified that error appears in the above-identified patent and that said Letters Patent is hereby corrected as shown below:

In the Claims

At Column 12, Lines 2-3, in Claim 3, the word "bacterium" should be deleted.

Signed and Sealed this
Sixth Day of June, 2023

Katherine Kelly Vidal
*Director of the United States Patent and Trademark Office*